A

US007611695B2

(12) United States Patent
Allred

(10) Patent No.: US 7,611,695 B2
(45) Date of Patent: Nov. 3, 2009

(54) FLAVORED HEMOSTATIC AND ACID ETCHING COMPOSITIONS

(75) Inventor: Peter M. Allred, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 327 days.

(21) Appl. No.: 10/988,872

(22) Filed: Nov. 15, 2004

(65) Prior Publication Data
US 2006/0104920 A1    May 18, 2006

(51) Int. Cl.
*A61K 8/00* (2006.01)
*A61C 5/02* (2006.01)
*A61K 33/00* (2006.01)
*A61K 33/06* (2006.01)
*A61K 33/26* (2006.01)

(52) U.S. Cl. .......... 424/49; 424/600; 424/647; 424/682; 424/685; 433/218; 433/228.1

(58) Field of Classification Search .......... 424/49
See application file for complete search history.

(56) References Cited

U.S. PATENT DOCUMENTS

| | | | | |
|---|---|---|---|---|
| 3,728,446 | A * | 4/1973 | Roberts et al. ............ | 424/49 |
| 4,551,100 | A | 11/1985 | Fischer ................ | 433/218 |
| 4,915,969 | A | 4/1990 | Beyts ................. | 426/548 |
| 4,976,954 | A * | 12/1990 | Kleber et al. ............. | 424/52 |
| 5,028,412 | A * | 7/1991 | Putt et al. .............. | 424/48 |
| 5,137,447 | A * | 8/1992 | Hunter ................. | 433/72 |
| 5,354,902 | A | 10/1994 | Merciadez et al. ......... | 562/601 |
| 5,374,659 | A * | 12/1994 | Gowan, Jr. ............... | 514/557 |
| 5,384,311 | A | 1/1995 | Antenucci et al. .......... | 514/53 |
| 5,385,727 | A | 1/1995 | Winston et al. ........... | 424/49 |
| 5,455,024 | A | 10/1995 | Winston et al. ........... | 424/52 |
| 5,455,285 | A | 10/1995 | Carroll ................ | 523/109 |
| 5,500,232 | A | 3/1996 | Keating ................ | 426/74 |
| 5,635,162 | A * | 6/1997 | Fischer ................ | 424/49 |
| 5,785,955 | A | 7/1998 | Fischer ................ | 424/49 |
| 5,895,641 | A | 4/1999 | Usen et al. ............. | 424/52 |
| 5,942,211 | A | 8/1999 | Harper et al. ............ | 424/49 |
| 5,993,880 | A | 11/1999 | Frost et al. ............. | 426/540 |
| 6,010,683 | A | 1/2000 | Fischer ................ | 424/52 |
| 6,013,294 | A | 1/2000 | Bunke et al. ............ | 426/120 |
| 6,083,489 | A | 7/2000 | Fischer et al. ........... | 424/52 |
| 6,121,315 | A | 9/2000 | Nair et al. .............. | 514/94 |
| 6,139,820 | A | 10/2000 | Fischer et al. ........... | 424/52 |
| 6,139,895 | A | 10/2000 | Zablocki et al. .......... | 426/573 |
| 6,159,448 | A | 12/2000 | Winston et al. ........... | 424/52 |
| 6,159,449 | A | 12/2000 | Winston et al. ........... | 424/52 |
| 6,165,512 | A | 12/2000 | Mezaache et al. ......... | 424/489 |
| 6,180,089 | B1 * | 1/2001 | Gambogi et al. .......... | 424/52 |
| 6,221,340 | B1 | 4/2001 | Yu et al. ............... | 424/49 |
| 6,235,322 | B1 | 5/2001 | Lederman .............. | 426/74 |
| 6,303,104 | B1 | 10/2001 | Winston et al. ........... | 424/49 |
| 6,312,671 | B1 | 11/2001 | Jensen et al. ............ | 424/53 |
| 6,322,774 | B1 | 11/2001 | Jensen et al. ............ | 424/53 |
| 6,372,198 | B1 | 4/2002 | Abbate ................ | 424/49 |
| 6,413,558 | B1 | 7/2002 | Weber et al. ............. | 426/2 |
| 6,432,415 | B1 * | 8/2002 | Osborne et al. ........... | 424/400 |
| 6,440,394 | B2 | 8/2002 | Barth et al. ............. | 424/48 |
| 6,451,290 | B2 | 9/2002 | Winston et al. ........... | 424/48 |
| 6,475,539 | B1 | 11/2002 | DeWillie et al. .......... | 426/72 |
| 6,494,716 | B1 * | 12/2002 | Dorn et al. ............. | 433/216 |
| 6,589,555 | B2 | 7/2003 | Pandya ................ | 424/466 |
| 6,638,918 | B2 * | 10/2003 | Davison et al. ........... | 514/55 |
| 6,689,343 | B1 | 2/2004 | Allred et al. ............ | 424/49 |
| 2002/0083955 | A1 * | 7/2002 | McDevitt et al. ......... | 132/321 |
| 2002/0169476 | A1 * | 11/2002 | Cohen ................ | 606/214 |

* cited by examiner

*Primary Examiner*—Frederick Krass
*Assistant Examiner*—Lezah W Roberts
(74) *Attorney, Agent, or Firm*—Workman Nydegger

(57) ABSTRACT

Hemostatic compositions and dental etching compositions for oral use include methyl salicylate in order to mask or disguise their otherwise unpleasant taste. The methyl salicylate, hemostatic and/or dental etching agent are dispersed within an aqueous carrier, which may be liquid or viscous as desired. In order to increase the stickiness and the viscosity of the carrier, a higher molecular weight polyol and/or a finely divided inorganic filler may be included. Methyl salicylate is selected as the flavorant because it has been found to have enhanced stability in the presence of strongly acidic compositions compared to other flavorants known in the art. In addition, methyl salicylate does not leave behind an unpleasant after taste. For this reason, methyl salicylate is uniquely suited for masking or disguising the profoundly sour, bitter and rusty taste of hemostatic agents or the sour or bitter taste of dental etching agents.

46 Claims, No Drawings

FLAVORED HEMOSTATIC AND ACID ETCHING COMPOSITIONS

CROSS-REFERENCE TO RELATED APPLICATIONS

Not applicable.

BACKGROUND OF THE INVENTION

1. The Field of the Invention

The present invention is in the field of hemostatic and acid etch compositions, more particularly hemostatic compositions for use in providing hemostasis in oral tissues and etching compositions used in etching teeth.

2. The Relevant Technology

In the course of performing certain dental procedures it is often desirable to use a hemostatic composition in order to stop the bleeding of oral tissues. For example, during dental reconstruction or preparation of dental crowns it is common for dentists to cut gingival or gum tissue in order to fully expose the tooth prior to taking an impression of the tooth. In order to make an accurate impression of the tooth it is advantageous for it to be clean and dry. For this reason, a hemostatic composition may be used to reduce or eliminate bleeding so that a more accurate impression of the patient's tooth can be taken.

In the case of invasive dental procedures, such as preparing the tooth to receive a crown or forming a deep dental preparation that is to be filled with a restorative composition, sufficient enamel and dentin may be removed so as to expose the pulp chamber. It may be desirable in some cases to apply a hemostatic composition to stop or slow bleeding of the exposed pulp.

Whereas hemostatic compositions of various types have been used successfully to stop or slow the bleeding of oral tissues during a variety of dental or oral procedures, hemostatic compositions can have a very unpleasant taste. Hemostatic compositions tend to be quite acidic (i.e., typically having a pH of about 1-2), which makes them have a profound sour or bitter flavor. They may also contain iron salts, which impart a rust-like flavor to the composition. It is therefore preferable to avoid contacting the patient's tongue with the hemostatic composition during the procedure in question. Allowing the hemostatic composition to contact the person's tongue is not only unpleasant to the patient, it may even cause the patient to flinch or experience a gag reflex, both of which can hinder the dental procedure.

A similar problem exists in the case of dental etching compositions used to etch a patient's tooth during a dental procedure. Dental etching compositions are typically used to create a superior bonding surface in dentin, enamel or both to which a restorative composition can better adhere. However, since dental etching compositions are by nature very acidic (i.e., typically having a pH of about 0-2), they also have a profound sour or bitter flavor and cause similar problems associated with hemostatic compositions. On the other hand, many flavorants are unstable in low pH compositions (e.g., due to acid catalyzed hydrolysis).

In view of the foregoing, it would be an advancement in the art to provide better tasting hemostatic and dental etching compositions.

SUMMARY OF THE INVENTION

The present invention is directed to hemostatic compositions and dental etching compositions that contain methyl salicylate as a flavorant to help mask the unpleasant taste of the hemostatic or etching agent. The pleasant taste imparted by methyl salicylate (i.e., that of wintergreen) reduces the chance that a patient will be surprised or startled in the event the hemostatic or dental etching composition were to contact the patient's tongue. Thus, an advantage of including methyl salicylate within such compositions is that it creates a more pleasant experience for the patient. It may also reduce the tendency of the patient to flinch or gag if the otherwise sour or bitter composition were to contact the patient's tongue.

An advantage of using methyl salicylate as a flavorant is that it has been found to be stable in the presence of hemostatic or dental etching agents, both of which are highly acidic in water. Thus, methyl salicylate is effective in disguising the sour or bitter taste of such agents even after being mixed and stored with such agents over time (e.g., weeks, months or even years). Methyl salicylate has also been found by the inventors to leave no bitter or unpleasant after taste.

Methyl salicylate and the hemostatic or dental etching agent are mixed together within an appropriate carrier, such as an aqueous liquid or gel. Water is typically used as part of the carrier in order to dissolve the hemostatic agent and/or dental etching agent within the carrier. Because methyl salicylate is sparingly soluble in water, organic solvents or liquids may be added to enhance the solubility of methyl salicylate. In the case where a sticky or viscous composition is desired, one or more thickening or tackifying agents may be included, examples of which include finely divided gel-forming metal oxides (e.g., filmed silica, precipitated or filmed aluminum oxide), organic thickeners (e.g., pemulen), or other gelling agents known in the art.

The inventive compositions may also include other adjuvents and active ingredients such as sweeteners (e.g., sucralose), carrier liquids (e.g., glycerine, polyethylene glycol, propylene glycol, and the like), desensitizing agents (e.g., $KNO_3$), anticariogenic agents (e.g., fluoride compounds), antimicrobial agents (e.g., antibiotics), stabilizing agents (e.g., EDTA), and the like. The carrier is preferably substantially free of abrasives.

Depending on the desired treatment regimen, the hemostatic or dental etching compositions according to the invention may vary as desired in potency, fluidity or stickiness in order to optimize the performance of the composition for a given treatment regimen.

Examples of hemostatic agents that may be used within the inventive hemostatic compositions include, but are not limited to, ferric sulfate, ferric subsulfate, ferric chloride, zinc chloride, aluminum chloride, aluminum sulfate, aluminum chlorohydrate, aluminum acetate, alum, salts of manganese, salts of bismuth, permanganates, and tannin.

Examples of dental etching agents include, but are not limited to, mineral acids, such as phosphoric acid, nitric acid, hydrochloric acid and sulfueric acid, and organic acids, such as glycolic acid, malic acid, maleic acid, acetic acid, citric acid, and EDTA.

Hemostatic compositions according to the invention will typically have a pH of less than about 3, preferably less than about 2.5, more preferably a pH less than about 2, and most preferably a pH in a range of about 1-2. Dental etching compositions according to the invention will typically have a pH of less than about 2.5, preferably less than about 2, more preferably a pH less than about 1, and most preferably a pH in a range of about 0-1.

These and other advantages and features of the present invention will become more fully apparent from the following description and appended claims, or may be learned by the practice of the invention as set forth hereinafter.

DETAILED DESCRIPTION OF THE PREFERRED EMBODIMENTS

I. Introduction

As summarized above, the invention is generally related to acidic hemostatic compositions and dental etching compositions that contain methyl salicylate, a flavorant that has been found to be stable in the presence of low pH hemostatic and/or etching agents and that tastes like wintergreen. The purpose of including methyl salicylate is to mask or disguise the unpleasant taste associated with hemostatic agents and/or dental etching agents. This, in turn, helps prevent patient gagging or flinching which improves the ability of the dentist to work on the patient's teeth.

Hemostatic compositions within the scope of the invention encompass virtually any hemostatic composition suitable for providing hemostasis in oral tissues so long as it contains methyl salicylate. Likewise, dental etching compositions within the scope of the invention encompass virtually any dental etching composition suitable for etching teeth so long as it contains methyl salicylate. The inventive compositions generally comprise at least one of a hemostatic agent or dental etching agent dispersed in an aqueous carrier. The carrier may be a liquid or gel and have any desired viscosity.

Examples of hemostatic compositions that have the consistency of a low viscosity liquid or fluid are Astringedent®, Astringedent® X, and Buffered Aluminum Chloride, which are sold by Ultradent Products, Inc., located in South Jordan, Utah. Examples of more viscous hemostatic compositions are ViscoStat® and ViscoStat® Plus, which are also available from Ultradent Products, Inc. Astringedent®, Astringedent® X, Buffered Aluminum Chloride, ViscoStat® and ViscoStat® Plus can be modified according to the teachings disclosed herein to include methyl salicylate in order to improve their taste.

Additional examples of hemostatic compositions that may be modified according to the present invention are set forth in U.S. Pat. No. 4,551,100 to Fischer, U.S. Pat. No. 5,635,162 to Fischer, and U.S. Pat. No. 5,785,955 to Fischer. For purposes of generally disclosing hemostatic compositions, the foregoing patents are incorporated herein by reference.

Examples of dental etching compositions that may be modified according to the invention so as to include methyl salicylate include Ultra-Etch® and Ultradent® Porcelain Etch, both of which are available from Ultradent Products, Inc.

The term "about" when used in combination with a numeric value shall mean±10% of the numeric value. Thus, the effect of the term "about" is to define a range that is +10% of the given numeric value.

II. Acidic Compositions Containing-Methyl Salicylate

The acidic dental compositions according to the invention include methyl salicylate, at least one acidic agent such as a hemostatic agent and/or a dental etching agent, and an aqueous carrier into which the methyl salicylate and acidic agent are dispersed. The compositions may include other ingredients as needed to yield a composition having desired properties. The acidic dental compositions are preferably formulated so as to be safe for introduction into the oral cavity of a patient.

A. Methyl Salicylate

Methyl salicylate is a colorless, yellowish, or reddish oily liquid, having the characteristic odor and taste of wintergreen. Synonyms of "methyl salicylate" include synthetic wintergreen oil; methyl hydroxybenzoate; betula oil; O-hydroxybenzoic acid methyl ester; gaultheria oil; methyl sweet birch oil; O-hydroxybenzoate; 2-(methoxycarbonyl)phenol; 2-carbomethoxyphenol; linsal; methylester kyseliny salicylove; salicylic acid methyl ester; and O-anisic acid.

The empirical formula of methyl salicylate is $C_6H_4(OH)COOCH_3$. The chemical structure of methyl salicylate is

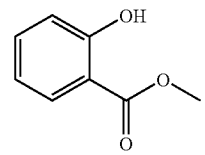

Methyl salicylate is soluble in alcohol, ether, acetone, glacial acetic acid, benzene, turpentine, boiling water, and is very slightly soluble in water. Methyl salicylate has a boiling point of 222° C.), a melting point of −8.3° C.), a flash point of 96° C., a specific gravity of 1.179-1.184, a vapor density of 5.24, and a refractive index of 1.535-1.538.

In general, the acidic compositions according to the invention will preferably contain methyl salicylate in an amount in a range of about 0.1% to about 20% by weight of the composition, more preferably in a range of about 0.5% to about 15% by weight of the composition, and most preferably in a range of about 1% to about 10% by weight of the composition.

The stability of methyl salicylate within the acidic compositions according to the invention is generally sufficient such that the acidic compositions can be stored for long periods of time and used as desired, while maintaining the flavor-imparting aspects of of the methyl salicylate so as to mask the generally sour, bitter and/or rusty taste of the hemostatic and/or dental etching agent. For example, acidic compositions containing methyl salicylate formed in accordance with the invention are likely after 1 year to still have substantially the same concentration of methyl salicylate as it contained when originally manufactured. In order to verify their longevity, compositions were stored for 3 years and then, when tested at periodic intervals of approximately every three months, were found to still have a noticeable wintergreen taste throughout the 3-year period.

In any event, the methyl salicylate content would be expected after 1 year to be at least 85% of the amount contained in the composition when initially manufactured. Similarly, the methyl salicylate content would be expected after about 4 to 6 months to be at least 90% of the amount contained in the composition when originally manufactured.

In any event, the ultimate shelf life of a particular composition according to the invention is not limited by the stability of the methyl salicylate within the composition. It is certainly the case that even if the methyl salicylate loses a significant or even a substantial portion of its flavor-imparting ability over time, the compositions will still function as intended even though they may begin to taste worse over time.

B. Hemostatic Agents

Hemostatic agents for use in the inventive compositions can be selected from a wide variety of hemostatic compounds or agents known in the art, which can be used singly or in a variety of different combinations. Examples include, but are not limited to, metal salts, such as the salts of aluminum, iron, zinc, manganese, and bismuth, as well as ions that contain one or more of these metals (e.g., permanganates).

Non-limiting examples of suitable hemostatic agents that may be used within hemostatic compositions within the scope of the invention include ferric sulfate, ferric subsulfate, ferric chloride, other iron (III) salts, zinc chloride, aluminum chloride, aluminum sulfate, aluminum chlorohydrate, aluminum acetate, alums (e.g., aluminum potassium sulfate and aluminum ammonium sulfate), tannins, and polyphenolic compounds.

A currently preferred hemostatic agent for use in formulating hemostatic compositions according to the invention is a ferric salt compound. Preferred ferric salts include ferric sulfate, which has the formula $Fe_2(SO_4)_3$, and ferric subsulfate, which has the formula $Fe_4(OH)_2(SO_4)_5$. Both ferric and sulfate ions are present within the human body. Thus, the probability of allergic reactions to ferric sulfate or ferric subsulfate is low. The ferric salts are coagulative hemostats, and when contacted with blood, the ferric salts cause an instant precipitation of blood proteins, which forms a coagulum.

The hemostatic agent may also facilitate tissue retraction by reducing the elasticity of collagen fibers within the gingival cuff. This can be beneficial in some cases as it can prevent premature closure of the sulcular space during impression placement and solidification. In addition, the hemostatic agent facilitates reduced sulcular fluid movement through intact epithelium, whether for impression making or during bonding or luting stages of the final restoration placement procedure. Finally, the hemostatic agent can be useful in stopping the bleeding of wounds in soft tissues in general.

When the acidic compositions according to the invention contain a hemostatic agent, the hemostatic agent is included in an effective amount so as to provide hemostatic properties to the composition. The hemostatic agent is preferably included within the hemostatic composition in an amount in a range of about 1% to about 40% by weight of the hemostatic composition, more preferably in a range of about 5% to about 35% by weight, and most preferably in a range of about 10% to about 30% by weight of the hemostatic composition.

Hemostatic compositions according to the invention will typically have a pH of less than about 3, preferably less than about 2.5, more preferably less than about 2, and most preferably have a pH in a range of about 1 to about 2.

C. Dental Etching Agents

Dental etching agents for use in the inventive compositions can be selected from a wide variety of acidic compounds that are capable of etching. Examples of dental etching agents include, but are not limited to, mineral acids, such as phosphoric acid, nitric acid, hydrochloric acid and sulfuric acid, and organic acids, such as glycolic acid, malic acid, maleic acid, acetic acid, citric acid, and EDTA.

When the acidic compositions according to the invention contain a dental etching agent, the etching agent is included in an effective amount so as to etch at least one of dentin or enamel. The etching agent is preferably included within the dental etching composition in an amount in a range of about 10% to about 60% by weight of the etching composition, more preferably in a range of about 20% to about 50% by weight, and most preferably in a range of about 25% to about 45% by weight of the etching composition.

Dental etching compositions within the scope of the invention will preferably have a pH of less than about 2, more preferably less than about 1, and most preferably have a pH in a range of 0 to about 1.

D. Carrier

The compositions according to the invention typically include an aqueous carrier. The water can be present as part of the other components of the composition or it can be added separately. The water may be deionized if desired prior to use in the composition. In general, water is included in an amount in a range from about 1% to about 80% by weight of the acidic composition, more preferably in a range of about 40% to about 60% by weight.

The various components may be mixed together in the desired amounts using standard mixing procedures to form the composition of the invention. If a solid hemostatic agent, such as a solid ferric salt, is used in formulating the compositions according to the invention, it is preferably to first dissolve the solid hemostatic agent in water before adding the other components of the composition.

Various polyols can be added to the compositions according to the invention. Examples of suitable polyols include polyethylene glycol, glycerin, propylene glycol, dipropylene glycol, polypropylene glycol, sorbitol, and the like. Polyols can be added to enhance the solubility of methyl salicylate in water. In addition, the polyols used can have a wide variety of molecular weights, with higher molecular weight polyols generally increasing the viscosity of the acidic compositions according to the invention. For example, polyols having an average molecular weight (number average) of at least about 600 may be included in order to increase the viscosity of the resulting composition. It should be understood that polyols having an average molecular weight of up to 100,000 or more may also be used. In some cases it may be desirable to mix two or more different polyols together having different molecular weights in order to yield a composition having the desired properties. When a polyol is included within the composition according to the invention, they are preferably included in an amount in a range from about 0.1% to about 50% by weight of the composition, and more preferably in a range of about 5% to about 40% by weight.

It is within the scope of the invention to include one or more thickening agents within the compositions according to the invention in order to yield a composition having the desired viscosity and/or thixotropic nature. Higher molecular weight polyols are examples of thickening agents that may be used in accordance with the invention. An organic polymer thickening agent that is relatively stable in the presence of weakly acidic compositions is pemulen, a high molecular weight, cross linked copolymer of acrylic acid and a hydrophobic comonomer. Other polymeric thickening agents may be used with the caveat that many thickening agents tend to break down and are unstable in the presence of strong acids.

Accordingly, it may be desirable to instead include inorganic fillers, preferably finely divided organic particulate fillers that are able to impart a thickening effect. Examples of inorganic fillers that may be used to impart a thickening effect include silica-based particulates such as colloidal silica, fumed silica, ground silica, precipitated silica, and the like. Silica-based fillers are able to provide a thixotropic property to the compositions, resulting in sheer thinning when agitated (such as when dispensed through a needle or agitated after being placed) and then thickening when agitation ceases, thereby resulting in a composition that becomes more viscous. This provides improved application control of the acidic compositions when applied using an applicator device such as the dento-infusor device as compared to non-viscous compositions it helps to keep the composition in place where applied.

Examples of other useful inorganic fillers include metal oxides such as aluminum oxide and titanium dioxide.

When an inorganic filler is included in the composition according to the invention, it is preferably included in an amount in a range from about 0.1% to about 30% by weight of the composition, more preferably in a range of about 0.1% to about 10% by weight.

E. Other Additives

The inventive compositions may also include other adjuvents and active ingredients such as sweeteners (e.g., sucralose), desensitizing agents (e.g., KNO$_3$), anticariogenic agents (e.g., fluoride compounds), antimicrobial agents (e.g., antibiotics), stabilizing agents (e.g. EDTA), and the like. The carrier is preferably substantially free of abrasives.

IV. EXAMPLES

The following examples set forth various exemplary hemostatic compositions and dental etching compositions according to the invention. These examples are intended to be purely exemplary and should not be viewed as limiting the scope of the present invention. Examples that were actually made are set forth in past tense, while hypothetical examples are set forth in present tense.

Example 1

A starting hemostatic composition was made by mixing the following ingredients in the amounts listed below:

| Ingredient | Amount (Weight %) |
| --- | --- |
| Ferric Sulfate | 34.4 |
| Deionized Water | 53.2 |
| Polyethylene Glycol (8000 m.w.) | 9 |
| Fumed Silica | 3.4 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 2

A starting hemostatic composition was made by mixing the following ingredients in the amounts listed below:

| Ingredient | Amount (Weight %) |
| --- | --- |
| Ferric Sulfate | 22.7 |
| Deionized Water | 47.9 |
| Polyethylene Glycol (8000 m.w.) | 26 |
| Fumed Silica | 3.4 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 3

A starting hemostatic composition was made by mixing the following ingredients in the amounts listed below:

| Ingredient | Amount (Weight %) |
| --- | --- |
| Ferric Sulfate | 20.6 |
| Deionized Water | 32.7 |
| Polyethylene Glycol (8000 m.w.) | 32.3 |
| Polyethylene Glycol (1450 m.w.) | 11.3 |
| Fumed Silica | 3.1 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 4

A starting hemostatic composition was made by mixing the following ingredients in the amounts listed below:

| Ingredient | Amount (Weight %) |
| --- | --- |
| Ferric Sulfate | 22.7 |
| Deionized Water | 52.9 |
| Polyethylene Glycol (8000 m.w.) | 21 |
| Fumed Silica | 3.4 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 5

A starting hemostatic composition was made by mixing the following ingredients in the amounts listed below:

| Ingredient | Amount (Weight %) |
|---|---|
| Aluminum Chloride | 22.7 |
| Deionized Water | 52.9 |
| Polyethylene Glycol (8000 m.w.) | 21 |
| Fumed Silica | 3.4 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 6

A starting hemostatic composition was made by mixing the following ingredients in the amounts listed below:

| Ingredient | Amount (Weight %) |
|---|---|
| Ferric Sulfate | 10 |
| Deionized Water | 77.6 |
| Polyethylene Glycol (8000 m.w.) | 2.4 |
| Fumed Silica | 10 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 7

A starting hemostatic composition was made by mixing the following ingredients in the amounts listed below:

| Ingredient | Amount (Weight %) |
|---|---|
| Ferric Sulfate | 34.4 |
| Deionized Water | 51.2 |
| Polyethylene Glycol (8000 m.w.) | 13.9 |
| Fumed Silica | 0.5 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 8

A starting hemostatic composition was made by mixing the following ingredients in the amounts listed below:

| Ingredient | Amount (Weight %) |
|---|---|
| Ferric Sulfate | 20 |
| Deionized Water | 65 |
| Fumed Silica | 15 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the oz concentration of methyl salicylate increases. The methyl salicylate remains stable for at least one year when the modified hemostatic compositions (pH<3) are stored at room temperature such that a substantial portion of the methyl salicylate still exists after one year.

Example 9

A starting hemostatic composition was made by mixing the following ingredients in the amounts listed below:

| Ingredient | Amount (Weight %) |
| --- | --- |
| Ferric Sulfate | 28 |
| Deionized Water | 63 |
| Fumed Silica | 9 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 10

A starting hemostatic composition was made by mixing the following ingredients in the amounts listed below:

| Ingredient | Amount (Weight %) |
| --- | --- |
| Ferric Sulfate | 20 |
| Deionized Water | 75 |
| Fumed Silica | 5 |

The pH of the starting, hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 11

A starting hemostatic composition was made by mixing the following ingredients in the amounts listed below:

| Ingredient | Amount (Weight %) |
| --- | --- |
| Ferric Sulfate | 18 |
| Deionized Water | 79 |
| Fumed Silica | 3 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 12

A starting hemostatic composition was made by mixing the following ingredients in the amounts listed below:

| Ingredient | Amount (Weight %) |
| --- | --- |
| Ferric Sulfate | 20 |
| Deionized Water | 54 |
| Fumed Silica | 26 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 13

A starting hemostatic composition was made by mixing the following ingredients in the amounts listed below:

| Ingredient | Amount (Weight %) |
| --- | --- |
| Aluminum Chloride | 18 |
| Deionized Water | 37 |
| Polyethylene Glycol (8000 m.w.) | 45 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room (temperature such that a substantial portion of the methyl salicylate still exists after one year.

Example 14

A starting hemostatic composition was made by mixing the following ingredients in the amounts listed below:

| Ingredient | Amount (Weight %) |
| --- | --- |
| Ferric Sulfate | 20 |
| Deionized Water | 54 |
| Polyethylene Glycol (8000 m.w.) | 26 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 15

A starting hemostatic composition was made by mixing the following ingredients in the amounts listed below:

| Ingredient | Amount (Weight %) |
| --- | --- |
| Ferric Sulfate | 15 |
| Deionized Water | 25 |
| Polyethylene Glycol (8000 m.w.) | 30 |
| Polyethylene Glycol (1500 m.w.) | 30 |

The pH of the starting hemostatic composition was less than 3. Modified hemostatic compositions are formed by adding methyl salicylate in varying amounts to the starting hemostatic composition in order to yield a plurality of modified hemostatic compositions that contain methyl salicylate in varying concentrations within a range of 0.1% to 20% by weight of the modified hemostatic compositions, with the concentration of methyl salicylate increasing by 0.1% increments throughout the range. At least some of the modified hemostatic compositions are subjectively better tasting than the starting hemostatic composition, with increasing wintergreen flavor as the concentration of methyl salicylate increases. The methyl salicylate remains stable for at least one year when the modified hemostatic compositions (pH<3) are stored at room temperature such that a substantial portion of the methyl salicylate still exists after one year.

Example 16

A hemostatic composition according to the invention was made by mixing together 94 parts by weight of Viscostat® (a 20% ferric sulfate hemostatic composition) available from Ultradent Products, Inc., 2 parts by weight of an aqueous sucralose solution (25% sucralose in water), and 4 parts by weight of methyl salicylate. The pH of the hemostatic composition was between 1 and 2. The resulting hemostatic composition was found to be better tasting than Viscostat® without methyl salicylate. The methyl salicylate remained stable for over one year in samples of the hemostatic composition that were stored at room temperature and at 37° C., respectively, such that the methyl salicylate was still able to impart a wintergreen taste after one year.

Example 17

A hemostatic composition according to the invention was made by mixing together 90 parts by weight of Viscostat®, 4 parts by weight of an aqueous sucralose solution (25% sucralose in water), and 6 parts by weight of methyl salicylate. The pH of the hemostatic composition was between 1 and 2. The resulting hemostatic composition was found to be better tasting than Viscostat® without methyl salicylate. The methyl salicylate remained stable for over one year in samples of the hemostatic composition that were stored at room temperature and at 37° C., respectively, such that the methyl salicylate was still able to impart a wintergreen taste after one year.

Example 18

A dental etching composition according to the invention was made by mixing together 94 parts by weight of Ultra-Etch® (a 35% phosphoric acid dental etching composition) available from Ultradent Products, Inc., 2 parts by weight of an aqueous sucralose solution (25% sucralose in water), and 4 parts by weight of methyl salicylate. The pH of the etching composition was between 0 and 1. The resulting etching composition was found to be better tasting than Ultra-Etch® without methyl salicylate. The methyl salicylate remained stable for over one year in samples of the etching composition that were stored at room temperature and at 37° C., respectively, such that the methyl salicylate was still able to impart a wintergreen taste after one year.

Example 19

A dental etching composition according to the invention was made by mixing together 96 parts by weight of Ultra-Etch®, 2 parts by weight of an aqueous sucralose solution (25% sucralose in water), and 2 parts by weight of methyl salicylate. The pH of the etching composition was between 0 and 1. The resulting etching composition was found to be better tasting than Ultra-Etch® without methyl salicylate. The methyl salicylate remained stable for over one year in samples of the etching composition that were stored at room temperature and at 37° C., respectively, such that the methyl salicylate was still able to impart a wintergreen taste after one year.

Example 20

A dental etching composition according to the invention was made by mixing together 93 parts by weight of Ultra-Etch®, 3 parts by weight of an aqueous sucralose solution (25% sucralose in water), and 4 parts by weight of methyl salicylate. The pH of the etching composition was between 0 and 1. The resulting etching composition was found to be better tasting than Ultra-Etch® without methyl salicylate. The methyl salicylate remained stable for over one year in samples of the etching composition that were stored at room temperature and at 37° C., respectively, such that the methyl salicylate was still able to impart a wintergreen taste after one year.

Example 21

A dental etching composition according to the invention was made by mixing together 90 parts by weight of Ultra-Etch®, 4 parts by weight of an aqueous sucralose solution (25% sucralose in water), and 6 parts by weight of methyl salicylate. The pH of the etching composition was between 0 and 1. The resulting etching composition was found to be better tasting than Ultra-Etch® without methyl salicylate. The methyl salicylate remained stable for over one year in samples of the etching composition that were stored at room temperature and at 37° C., respectively, such that the methyl salicylate was still able to impart a wintergreen taste after one year.

Example 22

A dental etching composition was made by mixing the following ingredients in the amounts listed below:

| Ingredient | Amount (Weight %) |
| --- | --- |
| Phosphoric acid (85% solution in water) | 15% |
| Glycolic acid | 6% |
| Sucralose (25% solution in water) | 2% |
| Water | 77% |

The pH of the dental etching composition was between 0 and 1. Modified dental etching compositions are formed by adding methyl salicylate in varying amounts to the starting etching composition in order to yield a plurality of modified etching compositions that contain methyl salicylate in varying concentrations within a range of 0.1% to 20% by weight of the modified etching compositions, with the concentration of methyl salicylate increasing by 0.1% increments throughout the range. The resulting etching compositions are better tasting than etching compositions that do not contain methyl salicylate. The methyl salicylate remains stable for over one year when stored at room temperature and is able to impart a wintergreen taste after one year.

Example 23

An etching composition was made by mixing the following ingredients in the amounts listed below:

| Ingredient | Amount (Weight %) |
| --- | --- |
| Phosphoric acid (85% solution in water) | 15% |
| Glycolic acid | 6% |
| Sucralose (25% solution in water) | 2% |
| Water | 75% |
| Nitric acid (1 Molar) | 2% |

The pH of the dental etching composition was between 0 and 1. Modified dental etching compositions are formed by adding methyl salicylate in varying amounts to the starting etching composition in order to yield a plurality of modified etching compositions that contain methyl salicylate in varying concentrations within a range of 0.1% to 20% by weight of the modified etching compositions, with the concentration of methyl salicylate increasing by 0.1% increments throughout the range. The resulting etching compositions are better tasting than etching compositions that do not contain methyl salicylate. The methyl salicylate remains stable for over one year when stored at room temperature and is able to impart a wintergreen taste after one year.

Example 23

Ultra-Etch® and Ultradent® Porcelain Etch are modified by adding methyl salicylate in varying amounts to the starting etching composition in order to yield a plurality of modified etching compositions that contain methyl salicylate in varying concentrations within a range of 0.1% to 20% by weight of the modified etching compositions, with the concentration of methyl salicylate increasing by 0.1% increments throughout the range. The resulting etching compositions are better tasting than etching compositions that do not contain methyl salicylate. The methyl salicylate remains stable for over one year when stored at room temperature and is able to impart a wintergreen taste after one year.

The acidic compositions according to the invention can be used in the same manner to treat teeth as hemostatic or dental etching compositions known in the art but which do not include methyl salicylate. Both viscous and non-viscous hemostatic or dental etching compositions can be used to stop bleeding during a wide variety of dental procedures.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hemostatic composition for use in providing hemostasis in oral tissues, comprising:
water;
an acidic agent comprising at least one hemostatic agent selected from the group consisting of iron (III) compounds, ferric sulfate, ferric subsulfate, ferric chloride, aluminum salts, zinc salts, manganese salts, bismuth salts, zinc chloride, aluminum chloride, aluminum sulfate, aluminum chlorohydrate, aluminum acetate, alum, permanganate, and tannin; and
methyl salicylate in an amount so as to impart a noticeable wintergreen taste,
the hemostatic composition having a pH of less than 2.

2. A hemostatic composition as defined in claim 1, the hemostatic agent comprising at least one iron (III) compound.

3. A hemostatic composition as defined in claim 2, the iron (III) compound comprising at least one of ferric sulfate, ferric sub sulfate or ferric chloride.

4. A hemostatic composition as defined in claim 1, the hemostatic agent comprising at least one salt of aluminum, zinc, manganese or bismuth.

5. A hemostatic composition as defined in claim 1, the hemostatic agent comprising at least one of zinc chloride, aluminum chloride, aluminum sulfate, aluminum chlorohydrate, aluminum acetate, alum, permanganate, or tannin.

6. A hemostatic composition as defined in claim 1, the hemostatic agent having a concentration in a range of about 1% to about 40% by weight of the hemostatic composition.

7. A hemostatic composition as defined in claim 1, the hemostatic agent having a concentration in a range of about 5% to about 35% by weight of the hemostatic composition.

8. A hemostatic composition as defined in claim 1, the hemostatic agent having a concentration in a range of about 10% to about 30% by weight of the hemostatic composition.

9. A hemostatic composition as defined in claim 1, the hemostatic composition having a pH in a range of about 1 to 2.

10. A hemostatic composition as defined in claim 1, the acidic agent further comprising at least one dental etching agent.

11. A hemostatic composition as defined in claim 10, the dental etching agent comprising at least one component selected from the group consisting of mineral acids, phosphoric acid, nitric acid, hydrochloric acid, and sulfuric acid.

12. A hemostatic composition as defined in claim 10, the dental etching agent comprising at least one component selected from the group consisting of organic acids, glycolic acid, malic acid, maleic acid, acetic acid, citric acid, and EDTA.

13. A hemostatic composition as defined in claim 10, the dental etching agent having a concentration in a range of about 10% to about 60% by weight of the hemostatic composition.

14. A hemostatic composition as defined in claim 10, the dental etching agent having a concentration in a range of about 20% to about 50% by weight of the hemostatic composition.

15. A hemostatic composition as defined in claim 10, the dental etching agent having a concentration in a range of about 25% to about 45% by weight of the hemostatic composition.

16. A hemostatic composition as defined in claim 10, the hemostatic composition having a pH of about 1, or less than 1.

17. A hemostatic composition as defined in claim 1, the methyl salicylate having a concentration in a range of about 0.1% to about 20% by weight of the hemostatic composition.

18. A hemostatic composition as defined in claim 1, the methyl salicylate having a concentration in a range of about 0.5% to about 15% by weight of the hemostatic composition.

19. A hemostatic composition as defined in claim 1, the methyl salicylate having a concentration in a range of about 1% to about 10% by weight of the hemostatic composition.

20. A hemostatic composition for use in providing hemostasis in oral tissues, comprising:
water;
at least one hemostatic agent in a range of about 5% to about 30% by weight of the hemostatic composition; and
methyl salicylate in a range of about 0.1% to about 20% by weight of the hemostatic composition,
the hemostatic composition having a pH of less than 2.

21. A hemostatic composition as defined in claim 20, the hemostatic agent comprising at least one iron (III) compound.

22. A hemostatic composition as defined in claim 21, the iron (III) compound comprising at least one of ferric sulfate, ferric subsulfate, or ferric chloride.

23. A hemostatic composition as defined in claim 20, the hemostatic agent comprising at least one salt of aluminum, zinc, manganese or bismuth.

24. A hemostatic composition as defined in claim 20, the hemostatic agent comprising at least one of zinc chloride, aluminum chloride, aluminum sulfate, aluminum chlorohydrate, aluminum acetate, alum, permanganate, or tannin.

25. A hemostatic composition as defined in claim 20, the methyl salicylate having a concentration in a range of about 0.5% to about 15% by weight of the hemostatic composition.

26. A hemostatic composition as defined in claim 20, the methyl salicylate having a concentration in a range of about 1% to about 10% by weight of the hemostatic composition.

27. A hemostatic composition as defined in claim 20, further comprising at least one thickening agent.

28. A hemostatic composition as defined in claim 27, the thickening agent comprising at least one particulate filler.

29. A hemostatic composition as defined in claim 27, the thickening agent comprising at least one of fumed silica, colloidal silica, precipitated silica, ground silica, fumed aluminum oxide, or titanium dioxide.

30. A hemostatic composition as defined in claim 27, the thickening agent comprising at least one polymeric thickening agent.

31. A hemostatic composition as defined in claim 20, further comprising at least one polyol.

32. A hemostatic composition as defined in claim 31, the polyol having a molecular weight of about 600, or more than 600.

33. A hemostatic composition as defined in claim 31, the polyol comprising at least one of polyethylene glycol or polypropylene glycol.

34. An oral composition for use in providing hemostasis in oral tissues or in etching teeth, comprising:
water;
an acidic agent comprising at least one of a hemostatic agent or a dental etching agent; and
methyl salicylate included as the sole flavorant in the oral composition in an amount so as to impart a noticeable wintergreen taste,
the oral composition having a pH of less than 1,
wherein the oral composition is free of abrasives, and
wherein the oral composition is free of sweeteners.

35. An oral composition as defined in claim 34, the dental etching agent comprising at least one mineral acid.

36. An oral composition as defined in claim 35, the mineral acid comprising at least one of phosphoric acid, nitric acid, hydrochloric acid, or sulfuric acid.

37. An oral composition as defined in claim 34, the dental etching agent comprising at least one organic acid.

38. An oral composition as defined in claim 37, the organic acid comprising at least one of glycolic acid, malic acid, maleic acid, acetic acid, citric acid, or EDTA.

39. An oral composition as defined in claim 34, the dental etching agent having a concentration in a range of about 10% to about 60% by weight of the oral composition.

40. An oral composition as defined in claim 34, the dental etching agent having a concentration in a range of about 20% to about 50% by weight of the oral composition.

41. An oral composition as defined in claim 34, further comprising at least one thickening agent.

42. An oral composition as defined in claim 41, the thickening agent comprising at least one particulate filler.

43. An oral composition as defined in claim 41, the thickening agent comprising at least one polymeric thickening agent.

44. A one-part dental etching composition for use in etching teeth, comprising:
water;
a dental etching agent comprised of at least one organic acid; and
methyl salicylate in a range of about 1% to about 10% by weight of the dental etching composition,
the oral composition having a pH of about 2, or less than 2,
wherein the dental etching composition is free of abrasives.

45. A one-part dental etching composition as defined in claim 44, wherein the dental etching composition has a pH of less than 2.

46. A hemostatic composition for use in providing hemostasis in oral tissues, comprising:
  water;
  an acidic agent comprising at least one hemostatic agent selected from the group consisting of iron (III) compounds, ferric sulfate, ferric subsulfate, ferric chloride, zinc salts, manganese salts, bismuth salts, zinc chloride, permanganate, and tannin; and
  methyl salicylate in an amount so as to impart a noticeable wintergreen taste,
  the hemostatic composition having a pH of about 2, or less than 2.

* * * * *

UNITED STATES PATENT AND TRADEMARK OFFICE
CERTIFICATE OF CORRECTION

PATENT NO. : 7,611,695 B2 Page 1 of 1
APPLICATION NO. : 10/988872
DATED : November 3, 2009
INVENTOR(S) : Allred It is certified that error appears in the above-identified patent and that said Letters Patent is hereby corrected as shown below:

Column 2
Line 18, change "after taste" to --aftertaste--
Line 53, change "sulfueric" to --sulfuric--

Column 3
Line 50, change "+" to --±--

Column 10
Line 58, delete "oz"

Column 13
Line 7, delete "("

Column 16
Line 60, change "sub sulfate" to --subsulfate--

Signed and Sealed this

First Day of June, 2010

David J. Kappos
*Director of the United States Patent and Trademark Office*